(12) United States Patent
Obradovic

(10) Patent No.: US 11,738,178 B2
(45) Date of Patent: *Aug. 29, 2023

(54) EXPANDABLE INTRODUCER SHEATH

(71) Applicant: Bentley InnoMed GmbH, Hechingen (DE)

(72) Inventor: Milisav Obradovic, Lorrach (DE)

(73) Assignee: Bentley InnoMed GmbH, Hechingen (DE)

( * ) Notice: Subject to any disclaimer, the term of this patent is extended or adjusted under 35 U.S.C. 154(b) by 840 days.

This patent is subject to a terminal disclaimer.

(21) Appl. No.: 16/719,495

(22) Filed: Dec. 18, 2019

(65) Prior Publication Data

US 2020/0139089 A1    May 7, 2020

Related U.S. Application Data

(63) Continuation of application No. 15/509,439, filed as application No. PCT/EP2015/072227 on Sep. 28, 2015, now Pat. No. 10,543,342.

(30) Foreign Application Priority Data

Sep. 26, 2014   (DE) ..................... 10 2014 014 015.6

(51) Int. Cl.
*A61M 25/06* (2006.01)
*A61M 25/00* (2006.01)

(52) U.S. Cl.
CPC .... *A61M 25/0662* (2013.01); *A61M 25/0023* (2013.01); *A61M 25/0054* (2013.01); *A61M 2025/0024* (2013.01)

(58) Field of Classification Search
CPC .......... A61M 25/0062; A61M 25/0054; A61M 25/0023; A61M 25/0024
See application file for complete search history.

(56) References Cited

U.S. PATENT DOCUMENTS

| | | | |
|---|---|---|---|
| 10,543,342 B2* | 1/2020 | Obradovic | ........ A61M 25/0054 |
| 2002/0091355 A1 | 7/2002 | Hayden | |
| 2008/0140189 A1 | 6/2008 | Nguyen et al. | |
| 2008/0300544 A1 | 12/2008 | Palm | |

(Continued)

FOREIGN PATENT DOCUMENTS

| | | |
|---|---|---|
| DE | 102008011688 A1 | 9/2009 |
| JP | 2012075892 A | 4/2012 |
| WO | 2011/096975 A1 | 8/2011 |

OTHER PUBLICATIONS

Office Action dated Jan. 27, 2021 and issued in connection with related Indian Appl. No. 201747010184.

*Primary Examiner* — Laura A Bouchelle
*Assistant Examiner* — John A Doubrava
(74) *Attorney, Agent, or Firm* — Brooks Kushman P.C.

(57) ABSTRACT

The invention relates to an introducer sheath for catheters to be inserted into a vascular system comprising a connecting valve (2) and an insertion tube (3) having a proximal portion (4) and a distal portion (5), said distal portion (5) being of reduced diameter in comparison with the proximal portion (4), and to enable its diameter to be reversibly changed the insertion tube (3) is provided with longitudinally extending expansion elements with incisions (11, 11', 12) designed as predetermined breaking points.

11 Claims, 5 Drawing Sheets

(56) References Cited

U.S. PATENT DOCUMENTS

Figure 1:
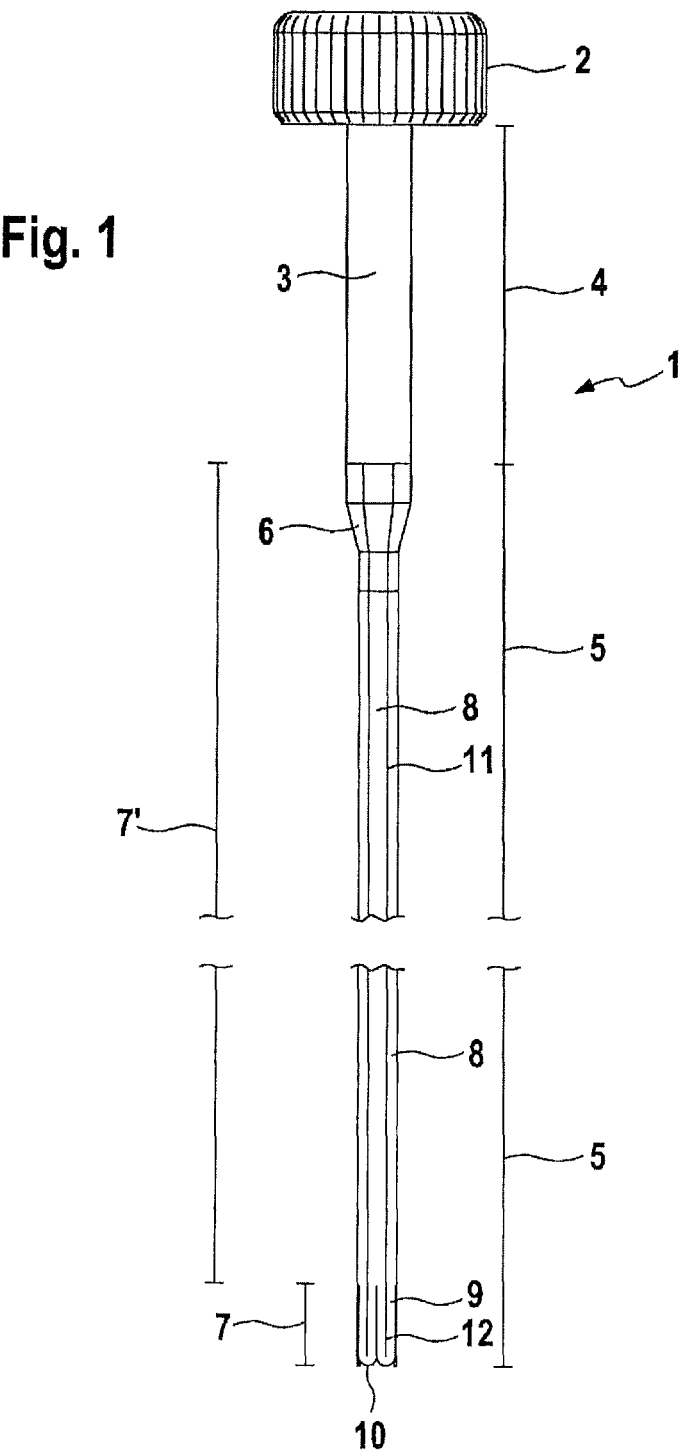

2011/0190683 A1* 8/2011 Gellman ........... A61M 25/0023
                                                        606/191
2013/0023734 A1   1/2013 Okamura
2014/0236088 A1* 8/2014 Al-Rashdan ...... A61M 25/0606
                                                        604/164.03

* cited by examiner

EXPANDABLE INTRODUCER SHEATH

The invention relates to an introducer sheath for catheters for insertion into a vascular system, said sheath comprising a connecting valve and an insertion tube having a proximal portion and a distal portion, said distal portion being of reduced diameter in comparison with the proximal portion.

Introducer sheaths are known that enable the vascular system to be accessed. They are needed if for an endovascular treatment a catheter has to be inserted into a vessel system via which implants or medical instruments are brought into the vascular system. Such introducer sheaths consist as a rule of plastic material, for example of polytetrafluoroethylene or other fluorinated polyolefins. In addition to providing access for a catheter introducer sheaths of this kind may also possess further means of entry that, for example, can be used for the introduction or aspiration of fluids.

It is frequently necessary during endovascular treatment to successively introduce into the vessel various medical devices of different size or diameter. Normally, introducing microcatheters by means of a guidewire is considered unproblematic; however, problems are encountered in the event of catheters of larger caliber as they are needed, for instance, for vessel dilatation, for the extraction of clots or for the implantation of large-caliber stents.

On the one hand, large-caliber introducer sheaths or insertion aids are difficult to navigate and, on the other, they often lead to injuries of the vessel wall and the tissue in the insertion zone when being removed. It has turned out to be of advantage to make use of introducer sheaths the inner diameter of which can be adapted to the relevant task or purpose, i.e. sheaths that are also suitable to accommodate catheters of large caliber and, moreover, that are capable of adjusting themselves to such large-size catheters. Nevertheless, problems may arise in the event the introducer sheaths having expanded to suit the required diameter maintain this expanded diameter even after the catheter has been removed.

It would thus be desirable for this reason to have available an introducer sheath capable of adjusting itself to the relevant catheter size needed in a given case but with said sheath reducing to the diameter originally arranged for after the catheter has been removed. After the treatment has been completed such an introducer sheath can be retracted quite easily and with only minimum risks of causing injuries to the vascular system.

This objective is reached by providing an introducer sheath of the kind first mentioned above, said sheath having an insertion tube enabling its diameter to be reversibly changed and having longitudinally extending expansion elements in which incisions are arranged designed as predetermined breaking points.

The introducer sheath proposed by the present invention for catheters to be placed into vascular systems is provided with a common connecting valve and an insertion tube. In the area of the connecting valve one or several additional accesses may be arranged which are preferably safeguarded by means of a Luer lock.

The insertion tube is divided into a proximal portion and a distal portion, with the diameter of the proximal portion being larger than that of the distal portion. The diameter of the distal portion enables customary small-caliber catheters to pass through. When placed in position the proximal portion of the introducer sheath is located in the access zone whereas the distal portion of the introducer sheath designed to offer the required flexibility is situated fully or for the main part in the vascular system. To facilitate the placement process the transitional zone between the proximal and the distal portion of the introducer sheath is of tapered design.

To enable large-caliber catheters to be introduced after having completed placement of the introducer sheath and insertion of a guidewire into the vascular system a plurality of longitudinally extending incisions are provided in the insertion tube, said incisions serving to reversibly change the tube diameter. Said incisions are designed such that they are capable of adjusting to a catheter of larger caliber and after the catheter has been removed cause the tube to reduce to its original diameter. In expanded state, the diameter of the insertion tube may increase by 200% or more with respect to its reduced state.

The incisions are so designed that they tear open when a catheter of larger caliber is being inserted, i.e. they are designed to serve as predetermined breaking points. To this end, the incisions preferably penetrate into the wall thickness of the 1o insertion tube down to approx. 25 to 95%. The incisions may be arranged on the inside or outside; however, arranging them on the outside is preferred. Usually, an incision depth of between approx. 60 and 90% of the wall thickness is considered sufficient.

Especially in its distal portion, the introducer sheath proposed by the present invention is provided with expansion elements. In any case, the expansion elements are also arranged over the preferably tapered transition area located between the proximal and distal portion. In this case, the expansion elements are equally spaced over the circumference of the insertion tube.

As per an embodiment of the invention the expansion elements are provided in the form of incisions which, however, do not extend over the entire length of the distal portion of the insertion tube.

In particular, the insertion tube is provided with two types of incisions of which first incisions extend from proximal to distal and terminate before the distal end of the insertion tube whereas second incisions which run from the distal end towards proximal extending merely over a distal area of the insertion tube. The second incisions may be provided in the form of slots fully penetrating through the wall.

In this manner, the distal portion of the introducer sheath is divided in a proximal area and a distal area, wherein the distal area denotes the zone through which the second incisions extend while the proximal area is to be understood as the zone proximally connecting to the proximal portion of the insertion tube. To the extent they also extend within the distal area the first incisions are preferably provided as well in the form of slots.

The first and second incisions are alternately arranged in the distal area of the insertion tube. This arrangement enables the second slots in the distal area of the insertion tube to form in expanded state a circumferential crown of meandering webs similar to the meandering structure of webs in a stent when expanded.

It is considered expedient to arrange an opening in the first incisions approximately at a location where the second incisions terminate, i.e. where the distal area of the insertion tube begins, said opening having a shape that roughly resembles an elongated diamond. This opening serves the purpose of facilitating the expansion of the insertion tube.

In accordance with another variant of the invention the expansion elements are incisions provided in the insertion tube surface, said incision extending in longitudinal direction alternately on the inside and outside. In this case, the depth of the incisions ranges between 50 and 80% of the wall thickness of the insertion tube, preferably between approx. 65 and 75%. Incisions of this configuration enable an accordionlike widening of the insertion tube when a large-caliber catheter is pushed through the tube. The amount by which the tube widens depends on the wall thickness, the depth of the incisions and the spacing of the incisions.

Incisions of this kind may extend over the entire length of the distal portion of the insertion tube. However, as provided for by an alternative, the incisions may only be arranged in the proximal area of the insertion tube while in the distal area the arrangement of slots as described hereinbefore is used according to which the slots in expanded state of the insertion tube form a circumferential crown of meandering webs. The number of incisions made in the proximal area of the insertion tube may in this case be considerably higher than the number of slots arranged in the distal area.

As per another variant of the invention the incisions of the expansion elements are provided in the form of slots also in the proximal area of the insertion tube, said slots fully cutting through the wall of the insertion tube. In this case as well the insertion tube can appropriately widen in the event a large-caliber catheter is introduced. When applying this variant it is to be noted, however, that when inserting the introducer sheath into the vascular system adequate sealing measures must be taken during the insertion phase since these slots are not capable of sealing the system effectively.

The invention is explained in more detail by way of the enclosed figures where

Figure 2:
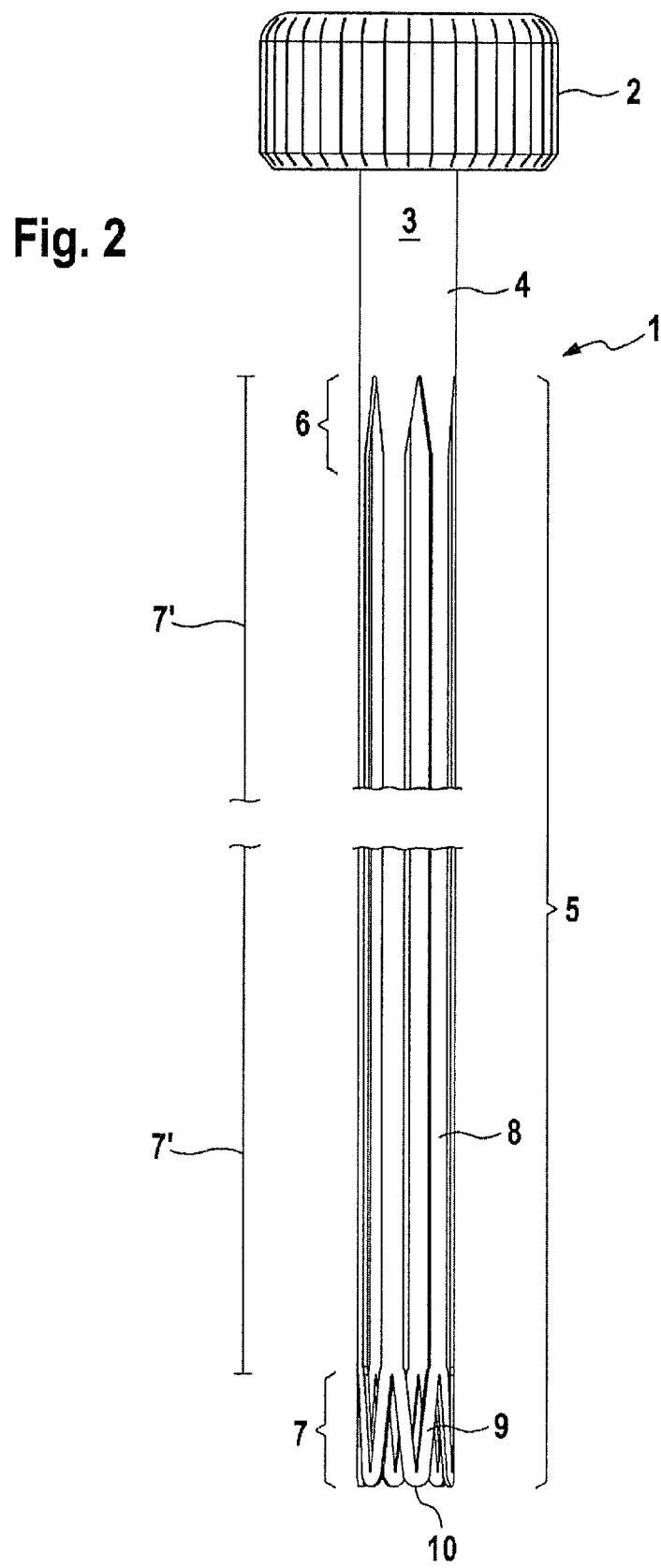
Figure 3:
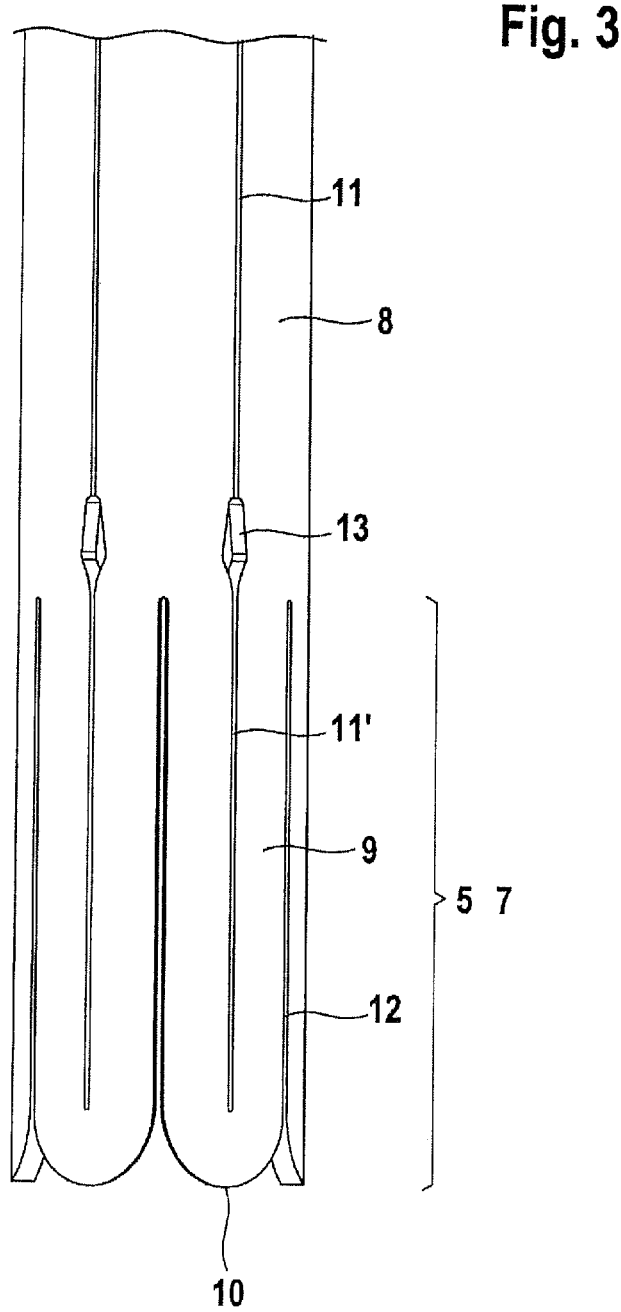
Figure 4:
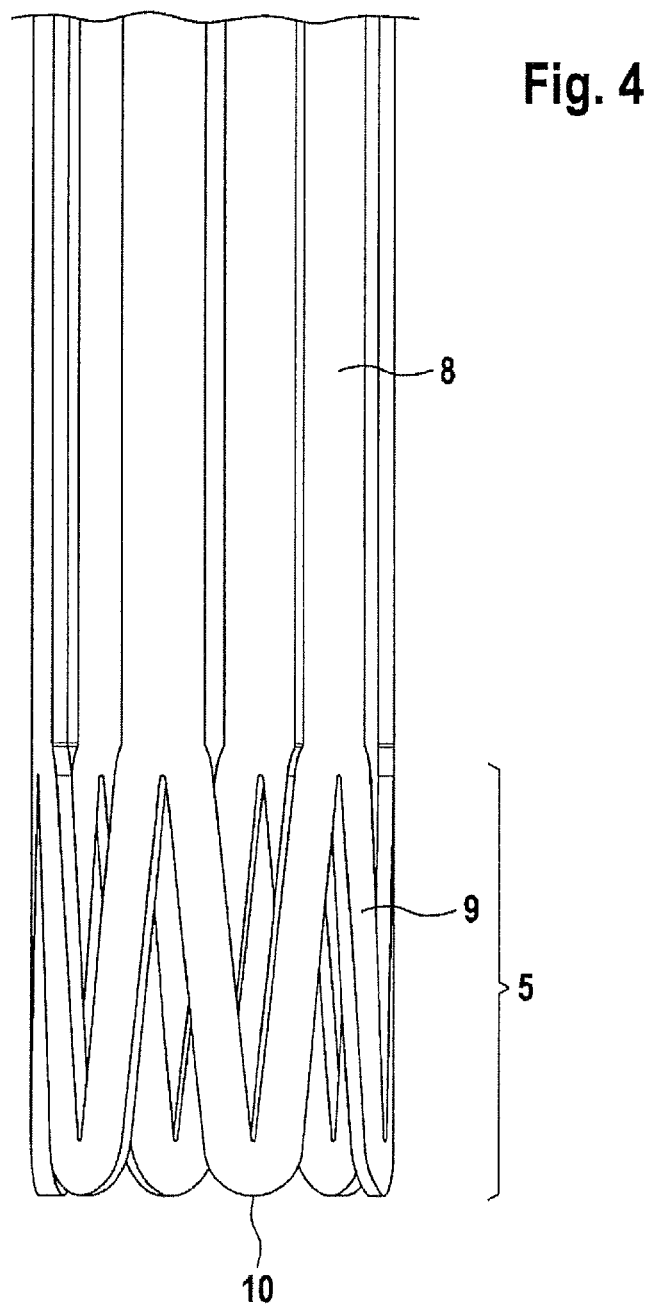
Figure 5:
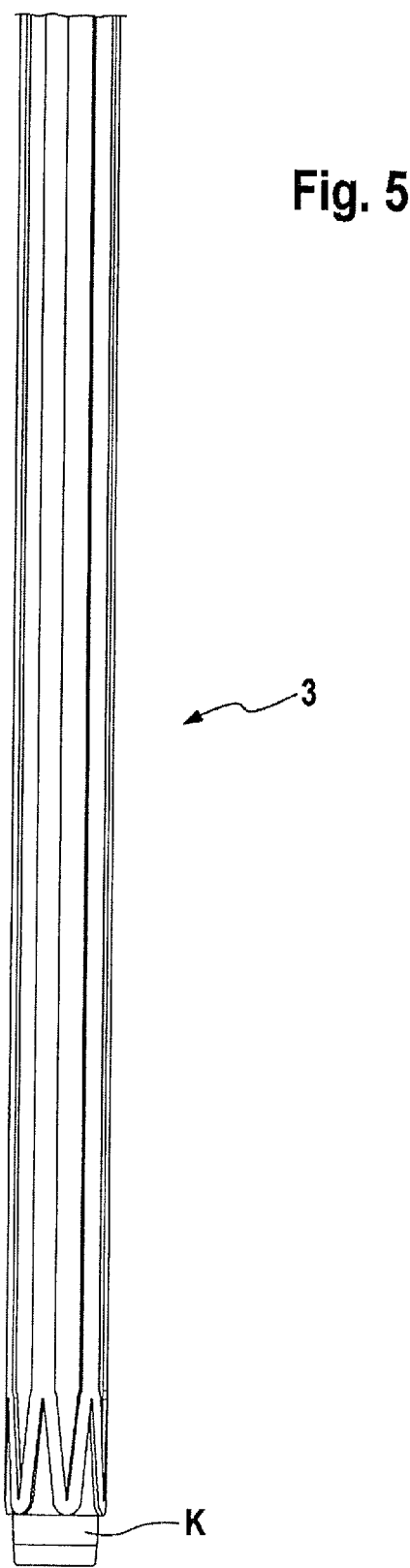

FIG. 1: shows an inventive introducer sheath in non-expanded state;

FIG. 2: depicts the introducer sheath shown in FIG. 1 in expanded state;

FIG. 3: illustrates the distal area of the insertion tube in non-expanded state;

FIG. 4: shows the distal area of the insertion tube in expanded state;

FIG. 5: shows the insertion tube in expanded state with a catheter inserted.

FIG. 1 illustrates an introducer sheath 1 proposed by the invention with the connecting valve 2 and insertion tube 3. The insertion tube 3 itself is divided into a proximal portion 4 with fixed diameter and a distal portion 5 which is of variable diameter as a result of the arranged expansion elements. Moreover, the distal portion 5 of the insertion tube 3 is divided into a distal area 7 and proximal area 7' located above and adjacent to the proximal portion 4. In this way, the proximal and distal areas of the insertion tube are complementary in forming distal portion 5.

In the distal portion of the insertion tube there are longitudinally extending incisions 11 together with webs 8. Incisions 11 are equally distributed over the circumference of the insertion tube 3. Incisions 11 are also arranged in the transitional zone 6 which has a tapered shape. In the transitional area 6 which is considered to form part of distal portion 5 the inner and outer diameter of the proximal portion 4 reduces to that of the distal area 5.

Incisions 11 represent the first incisions extending from the proximal end of the distal portion 5 to just before the distal end of the distal portion 5. In the distal area 7 the incisions 11 are preferably designed in the form of slots 11'. In the distal area 7 between the first incisions 11 and 11' there are second incisions 12 which are also designed in the form of slots, they are also regularly spaced and extend from the distal end 10 over the entire distal area 7. The alternating arrangement of the first and second incisions in distal area 7 allows the formation of a crown of meandering webs that occupies the entire distal area 7. At the distal end 10 of the insertion tube 3 the webs are rounded so as to be atraumatic.

The expanded state of introducer sheath 1 in accordance with FIG. 1 is illustrated in FIG. 2. The incisions 11, 11', and 12 located between webs 8 and 9 are expanded and extend to shortly before the distal end 10 of insertion tube 3. In the distal area 7 of insertion tube 3 the web structure widens to form a meandering crown of webs, with the individual webs located between the second incisions 12 being of vee-shaped configuration. In the transitional area 6 of insertion tube 3 the expanded incisions 11 taper off until the normal diameter of the proximal portion 4 is reached.

Whereas incisions 11 in non-expanded state as illustrated in FIG. 1 do not yet fully cut through the tube wall in the proximal area 7' the incisions 11 in expanded state as shown in FIG. 2 are forced open and widened to form elongated interspaces. The incisions 11 are torn open when a large-caliber catheter is introduced. In the distal area 7 the slots 11' and 12 widen to form the vee-shaped interspaces located between webs 9 that constitute the crown of webs.

FIG. 3 is a detailed view of the insertion tube 3 showing distal area 7 and part of proximal area 7' arranged proximally adjacent to it, also incisions 11, 11', and 12 and the longitudinally extending webs 8 as well as webs 9 that when expanded form into a meandering configuration. The illustration shows the approximately diamond-shaped openings of first incisions 11 located in the transitional area towards distal area 7 as well as the rounded webs at the distal end 10 of insertion tube 3. It is to be noted that incisions 11' and 12 are designed as slots that fully cut through the wall.

FIG. 4 shows a detail of FIG. 3 in expanded state with the meandering crown of webs in distal area 5 and the parallelly extending webs located in the proximally adjacent area. The incisions 11, 11', and 12 are enlarged to form relatively wide interspaces.

In conclusion, FIG. 5 shows the expanded section of the insertion tube depicted in FIG. 4 with introduced catheter K that has caused expansion to take effect.

Retraction of the catheter upon completion of the respective treatment causes the insertion tube to be relieved of the expansion pressure so that it is able to contract and again assume its original diameter. As a result of this, the insertion tube can be drawn out and removed quite easily of its position in the tissue without the risk of causing tears or scissures in tissue and vessel wall.

The invention claimed is:

1. Introducer sheath for catheters to be inserted into a vascular system, said sheath comprising a connecting valve (2) and an insertion tube (3) having a proximal portion (4) and a distal portion (5), said distal portion (5) being of reduced diameter in comparison with the proximal portion (4), wherein the insertion tube (3), in order to enable its diameter to be reversibly changed, is provided with
   (i) longitudinally extending first expansion elements with first incisions (11, 11') designed as predetermined breaking points, said first incisions extending from the proximal end of the distal portion (5) to a position adjacent to the distal end of the distal portion (5);
   (ii) longitudinally extending second expansion elements with second incisions (12), said second incisions originating from the distal end (10) of the insertion tube (3) and extending in a distal area (7) of said tube.

2. Introducer sheath according to claim 1, characterized in that the incisions (11, 11', 12) are equally spaced over the circumference of the insertion tube (3).

3. Introducer sheath according to claim 1, characterized in that the incisions (11, 11', 12) are designed, at least partially, in the form of slots.

4. Introducer sheath according to claim 1, characterized in that the expansion elements are incisions (11, 11') that are alternately arranged on the inside and outside of the insertion tube (3).

5. Introducer sheath according to claim 3, characterized by first incisions (11, 11') and second incisions (12) in the distal portion (5) of the insertion tube (3), of which the first incisions (11, 11') extend from proximal to distal and the second incisions (12) run from the distal end towards proximal, wherein the areas located between the first (11, 11') and the second incisions (12) constitute webs (8, 9) of equal width.

6. Introducer sheath according to claim 5, characterized in that the first incisions (11') and second incisions (12) are alternately arranged in a distal area (7) of the insertion tube (3).

7. Introducer sheath according to claim 6, characterized in that the second incisions (12) in an expanded state of the insertion tube (3) form a circumferentially extending crown of meandering webs (8) in the distal area (7).

8. Introducer sheath according to claim 6, characterized in that the first incisions (11) at a transition zone from a proximal area (7') to the distal (7) area are provided with openings in the wall of the insertion tube (3).

9. Introducer sheath according to claim 4, characterized in that the depth of the incisions ranges between 25 and 95%, preferably 60 and 90% of the wall thickness of the insertion tube (3).

10. Introducer sheath according to claim 4, characterized in that the incisions (11, 11') extend over a proximal area (7') of the insertion tube (3).

11. Introducer sheath according to claim 10, characterized by first and second incisions (11', 12) in the distal area (7) of the insertion tube (3), said incisions forming webs (9) having a meandering configuration.

* * * * *